United States Patent [19]

Venkateswaran et al.

[11] Patent Number: 6,048,697
[45] Date of Patent: Apr. 11, 2000

[54] OLIGONUCLEOTIDES USED FOR DETECTING VIBRIO PARAHAEMOLYTICUS AND METHOD OF DETECTION THEREWITH

[75] Inventors: Kasthuri Venkateswaran, San Gabriel, Calif.; Nobuhiko Doumoto, Tokyo, Japan

[73] Assignee: Nippon Suisan Kaisha, Ltd., Tokyo, Japan

[21] Appl. No.: 09/155,200

[22] PCT Filed: Mar. 25, 1997

[86] PCT No.: PCT/JP97/00991

§ 371 Date: Jan. 6, 1999

§ 102(e) Date: Jan. 6, 1999

[87] PCT Pub. No.: WO97/35970

PCT Pub. Date: Oct. 2, 1997

[30] Foreign Application Priority Data

Mar. 26, 1996 [JP] Japan .................................. 8-095971

[51] Int. Cl.[7] .............................. C12Q 1/68; C12P 19/34; C07H 21/04
[52] U.S. Cl. ........................... 435/6; 435/91.2; 536/23.2; 536/23.7; 536/24.32; 536/24.33
[58] Field of Search ..................... 435/6, 91.2; 536/23.2, 536/23.7, 24.32, 24.33

[56] References Cited

FOREIGN PATENT DOCUMENTS

| 4-262799 | 9/1992 | Japan . |
| 5-123197 | 5/1993 | Japan . |
| 7-213299 | 8/1995 | Japan . |
| 7-114719 | 12/1995 | Japan . |

OTHER PUBLICATIONS

Dorsch, M. et al. Int. J. Systemic Bacteriology 42(1):58–63, Jan. 1992.

Lee, C. et al. J. Gen. Microbiology 139:3225–3231, Dec. 1993.

Jun Okuda et al., Microbial Pathogenesis 1995; 18:167–172.

Mitsuaki Nishibuchi et al., FEMS Microbiology Letters 67(1990) pp. 251–256.

Randall K. Saiki et al., Science (1988), vol. 239, No. 29, pp. 487–491.

Anita C. Wright et al., Applied and Environmental Microbiology, Feb. 1993, pp. 541–546.

Satoshi Yamamoto and Shigeaki Harayama, Applied and Environmental Microbiology, Mar. 1995, pp. 1104–1109.

*Primary Examiner*—Carla J. Myers
*Assistant Examiner*—Diana Johannsen
*Attorney, Agent, or Firm*—Armstrong, Westerman, Hattori, McLeland & Naughton

[57] ABSTRACT

An oligonucleotide is provided which has a nucleotide sequence derived from SEQ ID NO:1, characterized in that it contains at least one site capable of amplifying a nucleotide sequence characteristic of *Vibrio parahaemolyticus*. The oligonucleotide may have a nucleotide sequence not derived from SEQ ID NO:3, or incapable of amplifying nucleotide sequences originating in *Vibrio alginolyticus* and *Vibrio harveyi*, and may be represented by SEQ ID NO:5 or SEQ ID NO:6. A method of detecting *Vibrio parahaemolyticus* in a specimen is also provided which comprises preparing a primer set comprising two of the above oligonucleotides, selectively amplifying therewith a DNA gyrase subunit B gene sequence contained in the specimen as a target, and determining whether or not there is a gyrB unit specific for *Vibrio parahaemolyticus* in the specimen. Also provided is a primer which reacts specifically with a gyrB gene of *Vibrio parahaemolyticus* to thereby differentiate and identify the same among other Vibrios and strains other than the genus Vibrio. The *Vibrio parahaemolyticus*-specific primer serves to detect 285-bp gyrB gene fragments specific for this Vibrio by the PCR method without the necessity for DNA extraction or like operations from bacterial cells.

6 Claims, No Drawings

OLIGONUCLEOTIDES USED FOR DETECTING VIBRIO PARAHAEMOLYTICUS AND METHOD OF DETECTION THEREWITH

FIELD OF THE INVENTION

This invention relates to oligonucleotide primers for amplification of the target nucleotide sequence characteristic of Vibrio parahaemolyticus (abbreviated as "VP" somewhere hereinafter). This invention relates to the method for detecting Vibrio parahaemolyticus based on the polymerase chain reaction (PCR) using a primer specific for the DNA gyrase sub-unit B gene (Nucleotide sequence of DNA gyrase B subunit, abbreviated as "gyrB" hereinafter).

PRIOR ART

Vibrio parahaemolyticus is known to cause food poisoning in many countries. It is found not only in the intestine but also in other organs and in the postoperative wound. Vibrio parahaemolyticus is a Gram negative, polymorphic, bacilliform, halophilic, facultative anaerobe, which ferments carbohydrate to generate gas. It forms green colonies on thiosulfate-citrate-bile-sucrose (TCBS) agar.

For detection of Vibrio parahaemolyticus, is used usually a method where the specimen is cultivated in an enrichment medium followed by isolation by the selective plate culture. The conventional method of detection requires one week, and therefore a more rapid method has been desired.

The fluorescence assay based on determination of trypsin activity can detect rapidly Vibrio parahaemolyticus but cannot differentiate Vibrio parahaemolyticus from Vibrio alginolyticus or Vibrio harveyi. The conventional methods for identification of Vibrio parahaemolyticus and Vibrio alginolyticus are time-consuming because the 16S rRNA sequence reveals homology of 99.7% between Vibrio parahaemolyticus and Vibrio alginolyticus.

The genus Vibrio includes 37 different species, all of which are derived from aquatic environment. Based on the systematic data of rRNA, species known as V. angullarum, V. ordalli, and V. damsels have been newly classified as Listonella or Photobacterium. Ten species are involved in gastroenteritis, infection of the wound, and human septicemia, while 7 species are known to be pathogens for fish. Vibrio parahaemolyticus occurs usually in an environment such as river-mouth and sea, being isolated from sea water and fishes and shellfishes often in summer.

For isolation and identification of Vibrio parahaemolyticus, the specimen is inoculated into a selective medium such as the bromothymolblue-teepol agar medium or TCBS agar medium, followed by isolation of bluish green colonies and examinations for the biochemical properties of the colonies. Unfortunately many Vibrio species show the same responses, and thus more detailed biochemical examinations are required for reliable identification. Examinations for a variety of biochemical properties on many isolates are time-consuming and laborious. Serological identification of Vibrio parahaemolyticus shows a cross reaction with other Vibrio species.

A method for identification of a Vibrio species was developed which used DNA. In this method were used DNA probes capable of amplifying the cholera toxin operon from V. cholera 01 to identify specifically the bacterium. These probes cross-react with Vibrio species other than cholera toxin-producing V. cholera. A method for identification of V. vulnificus has been developed in which hybridization is carried out on a membrane filter by using a fluorescent-labeled oligonucleotide probe (Wright, A. C. et al., Appl. Environ. Microbiol. 59: 541–546, 1993).

In addition, the oligonucleotide DNA probe was constructed from a portion of the cytolysin gene (hlyA) sequence of V. vulnificus and labeled through the covalent bond. These probes do not react with non-toxinogenic V. vulnificus and therefore do not detect all strains of V. vulnificus.

Similarly, other molecular biologic methods using the toxic factor (TDH, TRH) genes as the target can detect toxinogenic V. parahaemolyticus, though based on the toxic factor, all strains of V. parahaemolyticus cannot be detected.

DISCLOSUR OF THE INVENTION

The object of this invention is to provide a method for differentiation of Vibrio parahaemolyticus from other 36 Vibrio species.

The object of this invention is to provide a method for detection of the 285-bp gyrB gene fragments specific for Vibrio parahaemolyticus by the PCR method without the necessity for DNA extraction or like operations from bacterial cells by use of Vibrio parahaemolyticus-specific primers.

Because this invention provides oligonucleotide probes useful for PCR, this invention relates to oligonucleotide primers for amplification of the target nucleotide sequence characteristic of Vibrio parahaemolyticus. The primers are exemplified by SEQ ID NO:5 and SEQ ID NO:6, which are used as a primer set for detection of the target nucleotide sequence characteristic of Vibrio parahaemolyticus.

The primer set is used in the method for determining whether or not there is the target nucleotide sequence characteristic of Vibrio parahaemolyticus. A Vibrio parahaemolyticus-specific primer is capable of detecting a Vibrio parahaemolyticus-specific gyrB gene fragment by the PCR method.

In this invention "primer" means an oligonucleotide which is produced synthetically or biologically and includes a specific nucleotide sequence which permits hybridization to a section containing the target nucleotide sequence.

A primer is capable of replicating a full target nucleotide sequence by synthesis by extension in the presence of polymerase or an analogous enzyme.

A primer is used in the method for amplification of nucleotide sequence, such as PCR and sequence displacement amplification (SDA) A particular primer, especially those useful for SDA technology, contains not only the sequence capable of hybridization to the target nucleic acid, but also a recognition sequence for restriction endonuclease and an arbitrary sequence which allows polymerase or another enzyme continuing polymerase-like activity to direct itself to initiate the synthesis of the template-specific oligonucleotide.

In this invention, "hybridization" means a process where, under pre-determined reaction conditions, partially or completely complementary nucleic acid chains, standing opposite to each other in an anti-parallel way, form a two-strand nucleic acid through specific and stable hydrogen bonds.

As described above, this invention relates to oligonucleotide primers useful for determination of the presence or absence of the target nucleotide sequence that is specific for Vibrio parahaemolyticus.

The procedures used for such determination include not only the PCR-based gene amplification procedure, but also Southern hybridization, a prior art, wherein the primer is used as a probe.

The primer in this invention is specific for the gyrB subunit gene sequence of *Vibrio parahaemolyticus*. The probe is specific for the internal consensus sequence in the primer amplification product.

The inventors have studied a method using the gyrB gene encoding the B subunit protein of DNA gyrase (topoisomerase II ) as a highly specific probe, to solve the problems in the prior art described above.

A method has been reported recently for detection and taxonomic analysis of *Pseudomonas putida* with a universal primer with which the gyrB gene was sequenced directly. Such universal primers were used for PCR-based amplification of the gyrB gene fragments of various Gram-negative and Gram-positive bacteria. The inventors used these existing primers to amplify the 1.2-kb gyrB fragments of 37 Vibrio species. The gyrB base sequence of *Vibrio parahaemolyticus* ATCC17802 and that of *Vibrio alginolyticus* ATCC17749 (abbreviated as 'VA' somewhere hereinafter) have been shown.

In addition, the inventors prepared PCR primers capable of amplifying and identifying only the gyrB gene of *Vibrio parahaemolyticus*. The sensitivity of these *Vibrio parahaemolyticus*-specific primers was investigated with 118 *Vibrio parahaemolyticus* strains, 20 *Vibrio alginolyticus* strains, and other 78 strains.

Yamamoto and Harayama (Appl. Environ. Microbiol. 61: 1104–1109, 1995) and others prepared PCR primers capable of amplifying the gyrB gene from two conserved regions of the amino acid sequences of the DNA gyrase subunit B proteins. These primers were used for amplification of the about 1.2-kb gyrB gene fragments from various bacteria.

The gyrB gene fragment amplified from *Vibrio parahaemolyticus* ATCC17802 and that from *Vibrio alginolyticus* AATCC17749 were cloned by using a suitable vector according to the conventional method of recombination (Sambrook et al., Molecular cloning: a laboratory manual, $2^{nd}$ ed., Cold Spring harbour Laboratory Press, Cold Spring Harbour, N.Y. 1989).

Desirable vectors include pGEMzf(+), and any common vector may be used.

The 1.2 kb gyrB gene fragment from *Vibrio parahaemolyticus* cloned with pGEMzf(+) is called a plasmid pVPgyrB, and that from *Vibrio alginolyticus* a plasmid pVAgyrB.

The probe is amplified also with a conventional method (Sambrook et al., 1989). For example, a plasmid is inserted into the vector for transformation of *Escherichia coli* with an effective mean such as calcium chloride. Transformed cells are cultivated under appropriate conditions.

The target genes are collected after lysis of bacterial cells, and purified by the alkali method or the like. Purified plasmid is used as the specimen.

The PCR method was tried for detection and differentiation of *Vibrio parahaemolyticus* from other Vibrio species including *Vibrio alginolyticus*. This method is capable of amplifying a sequence homologous with the probe, practically increasing the sensitivity.

According to the base sequence of the probe, the synthesized oligonucleotide primer amplifies DNA only when the target base sequence is present in the specimen. Not only the sensitivity is enhanced but also an absolute specificity can be attained by using an oligonulcleotide having specificity based on the base sequence of the DNA probe.

For preparation of effective primers, the base sequence of pVPgyrB and that of pVAgyrB were determined with the DNA sequencer according to the conventional method.

For determination of the base sequence of gyrB, the base sequence of the N-terminal and C-terminal regions of the amplified fragment was also determined by using UP-1S and UP-2Sr primers (Yamamoto and Harayama, Appl. Environ. Microbiol. 61: 1104–1109, 1995). For extension of the determined base sequence, an additional primer was prepared from the base sequence determined by using UP-1S. The length of the whole base sequence of the amplified fragment is 1258 bp, and the sequence is shown in SEQ ID NO:1 (pVPgyrB) and SEQ ID NO:3 (pVAgyrB). The amino acid sequence encoded by SEQ ID NO:1 and that encoded by SEQ ID NO:3 are shown in SEQ ID NO:2 and SEQ ID NO:4, respectively.

With this information of the base sequence, 21-bp primers were prepared that can detect and identify *Vibrio parahaemolyticus* from other bacteria. These primers contain SEQ ID NO:5 and SEQ ID NO:6, being usable as a primer set.

These novel primers are useful in the existing assay method using PCR (Saiki et al., Science 239: 487–491, 1988). These primers are used for amplification of the target DNA in a specimen, making the amount of DNA sufficient for detection. Following the amplification step, the step of detection may be performed by any method as far as it is effective for detection of DNA, for example, by electrophoresis on agarose gel.

The target DNA functions as the template. Amplification of the template DNA in the specimen is effected by treatment of the primer pair with a duplex DNA. This treatment results in extension of the sequence complementary to each nucleotide sequence. The resultant sequence functions as the template of the primer. The treatment process comprises denaturation of I)NA, annealing to a sequence complementary to the primer, and extension of the primer with DNA polymerase (e.g. Taq polymerase), and is repeated until DNA has been produced in an amount sufficient for detection of the target sequence. The conditions of the amplification based on PCR are summarized in the Example 3 below.

Following amplification, the amplified sequence is detected by electrophoresis on agarose gel. The primer pair [VP1 (SEQ ID NO:5), VP2 (SEQ ID NO:6)] amplifies the 285-bp when the gyrB gene sequence is used as the target.

The 285-bp DNA was amplified for 37 Vibrio strains obtained from ATCC, JCM, CDC, and NCIMB collections. The chromosomal DNA preparations from these bacteria were obtained according to the conventional method (Sambrook et al., Molecular cloning: a laboratory manual, $2^{nd}$ ed., Cold Spring Harbour Laboratory Press, Cold Spring Harbour, N.Y., 1989). The target DNA, 1 μg, was subjected to PCR. The 285-bp specific band was found only in the preparation from *Vibrio parahaemolyticus*, while it was not detected in any preparation from other species (Table 1). However the PCR-based amplification using the primer set (UP-1, UP-2r) according to Yamamoto and Harayama (1995) detected 1.2-kb gyrB fragment, and thus could confirm the presence of the DNA gyrase B subunit. Based on these findings, it is concluded that the primers of this invention are *Vibrio parahaemolyticus*-specific and usable for detection of the pathogen.

This invention relates to the oligonucleotides characterized in that they have the nucleotide sequence derived from Sequence No.1 and include at least one site capable of amplifying the Vibrio parahaemolyticus-specific nucleotide sequence. This invention relates to the oligonucleotides characterized in that they have the nucleotide sequence derived from SEQ ID NO:1 but not from SEQ ID NO:3 and include at least one site capable of amplifying the Vibrio parahaemolyticus-specific nucleotide sequence.

TABLE 1

| S.no. | Microbes | Strain Number | PCR results of gyrB 1.2-kb | 285bp |
|---|---|---|---|---|
| 1 | Vibrio aestuarianus | ATCC35048 | + | − |
| 2 | Vibrio albensis | ATCC14547 | + | − |
| 3 | Vibrio alginolyticus | ATCC17749 | + | − |
| 4 | Vibrio canipbelli | ATCC25920 | + | − |
| 5 | Vibrio carchariae | ATCC35084 | + | − |
| 6 | Vibrio cholerae 01 | P1418 | + | − |
| 7 | Vibrio choleraenon 01 | NR | + | − |
| 8 | Vibrio cincinnatiensis | ATCC35912 | + | − |
| 9 | Vibrio costicola | ATCC33508 | + | − |
| 1o | Vibrio diazotrophicus | ATCC33466 | + | − |
| 11 | Vibrio fischeri | ATCC 7744 | + | − |
| 12 | Vibrio fluvialis | JCM3752 | + | − |
| 13 | Vibrio furnissii | ATCC35016 | + | − |
| 14 | Vibrio gazogenes | ATCC29988 | + | − |
| 15 | Vibrio harveyi | ATCC14126 | + | − |
| 16 | Vibrio hollisae | CDC75-80 | + | − |
| 17 | Vibrio logei | ATCC29985 | + | − |
| 18 | Vibrio marinus | ATCC15381 | + | − |
| 19 | Vibrio mediterranei | ATCC43341 | + | − |
| 20 | Vibrio metschnikovii | ATCC 7708 | + | − |
| 21 | Vibrio mimicus | CNS9582 | + | − |
| 22 | Vibrio mytili | NCIMB13275 | + | − |
| 23 | Vibrio natriegens | ATCC14048 | + | − |
| 24 | Vibrio navarrensis | NCIMB13120 | + | − |
| 25 | Vibrio nereis | ATCC25917 | + | − |
| 26 | Vibrio nigripulchritudo | ATCC27043 | + | − |
| 27 | Vibrio ordalii | ATCC33509 | + | − |
| 28 | Vibrio orientalis | ATCC33934 | + | − |
| 29 | Vibrio parahaemolyticus | ATCC17802 | + | + |
| 30 | Vibrio proteolyticus | ATCC15338 | + | − |
| 31 | Vibrio salmonicida | ATCC43839 | + | − |
| 32 | Vibrio splendidus | ATCC33125 | + | − |
| 33 | Vibrio tubiashii | ATCC19109 | + | − |
| 34 | Vibrio vulnificus | ATCC 2046 | + | − |
| 35 | Listonella anguillarum | ATCC19264 | + | − |
| 36 | Listonella pelagia | ATCC25916 | + | − |
| 37 | Photohacterium damsela | ATCC33539 | + | − |

ATCC: American Type Culture Collection

JCM: Japan Collections of Microorganisms

NCIMB: National Collections of Industrial and Marine Bacteria

CDC: Centre for Disease Control

The symbols other than those described above refer to the strain names.

Also the standard strains of genera Aeromonas, Alteromonas, Marinomonas, Shigella, Shewanella, Salmonella, Escherichia and Staphylococcus aureus were examined for the presence of gyrB and the Vibrio parahaemolyticus-specific 285-bp. As shown in Table 2, gyrB was found to be present in all of the strains though the Vibrio parahaemolyticus-specific 285-bp amplification was found in none of the strains.

TABLE 2

| S.no. | Microbes | Strain number | PCR results of gyrB 1.2-kb | 285bp |
|---|---|---|---|---|
| 1 | Alteromonas atlantica | ATCC19262 | + | − |
| 2 | Alteromonas carrogeenovara | ATCC43555 | + | − |
| 3 | Alteromonas citrea | ATCC29719 | + | − |
| 4 | Alteromonas espejiana | ATCC29659 | + | − |
| 5 | Alteromonas haloplanktis | ATCC14393 | + | − |
| 6 | Alteromonas luteoviolaceae | ATCC33492 | + | − |
| 7 | Alteromonas macleodii | ATCC27126 | + | − |
| 8 | Alteromonas tetraodonis | NCIMB13177 | + | − |
| 9 | Alteromonas undina | ATCC29660 | + | − |
| 10 | Marinomonas communis | ATCC27118 | + | − |
| 11 | Marinomonas vaga | ATCC27119 | + | − |
| 12 | Aeromonas hydrophila | ATCC19570 | + | − |
| 13 | Esherichia coli | ATCC25922 | + | − |
| 14 | Salmonella typhimurium | ATCC13311 | + | − |
| 15 | Shewanella putrefaciens | ATCC 8071 | + | − |
| 16 | Shigella dysenteriae | ATCC13313 | + | − |
| 17 | Shigella sonneii | ATCC29930 | + | − |
| 18 | Staphylococcus aureus | ATCC12600 | + | − |

Various phenotypes, serotypes, and toxinogenic types have been reported for Vibrio parahaemolyticus. A probe specific for the thermostable hemolysin, a toxin produced by Vibrio parahaemolyticus, has been reported (Nishibuchi et al., FEMS Microbiol. Lett. 55: 251–256, 1990). Such toxin-specific probes are clinically important, though they cannot detect all types of Vibrio parahaemolyticus. For prevention of contamination of food with Vibrio parahaemolyticus, it is essential to detect all types of Vibrio parahaemolyticus in food or in the environment. Then Vibrio parahaemolyticus strains isolated from food, water, soil, and other materials were investigated for their phenotypes, serotypes, and the toxicity. All of the 118 Vibrio parahaemolyticus strains were subjected to PCR using the primers VP1 and VP2. It was evident that the 285-bp had been amplified.

The results are summarized in Table 3. The strains shown in Table 3 are those isolated from and identified in food, soil, water or feces, some of which were kindly given by Prof. Shinoda, Okayama University, and Prof. Yamamoto, Kyushu University. As shown in Table 3, amplification of the 285-bp was not observed in any of the 20 strains of Vibrio alginolyticus also isolated from various materials.

This invention relates to oligonucleotides characterized in that they have the nucleotide sequence obtained from SEQ ID NO:1, contain at least one site capable of amplifying the nucleotide sequence characteristic of Vibrio parahaemolyticus, and cannot amplify the nucleotide sequence derived from Vibrio alginolyticus or Vibrio harvei.

This invention relates to oligonucleotides characterized in that they have the nucleotide sequence obtained from SEQ ID NO:1 but not from SEQ ID NO:3, contain at least one site capable of amplifying the nucleotide sequence characteristic of Vibrio parahaemolyticus, and cannot amplify the nucleotide sequence derived from Vibrio alginolyticus or Vibrio harvei.

TABLE 3

| S.no. | Name | Strain no. | Kanagawa phenomenon | PCR |
|---|---|---|---|---|
| 1 | V. parahaemolyticus | 33-7 | + | + |
| 2 | V. parahaemolyticus | 33-8 | + | + |
| 3 | V. parahaemolyticus | 33-10 | + | + |
| 4 | V. parahaemolyticus | V83 | + | + |

TABLE 3-continued

| S.no. | Name | Strain no. | Kanagawa phenomenon | PCR |
|---|---|---|---|---|
| 5 | V. parahaemolyticus | WP-1(y) | + | + |
| 6 | V. parahaemolyticus | WP-1 | + | + |
| 7 | V. parahaemolyticus | 39-11 | − | + |
| 8 | V. parahaemolyticus | 46-11 | − | + |
| 9 | V. parahaemolyticus | AQ3301 | − | + |
| 1o | V. parahaemolyticus | AQ3314 | − | + |
| 11 | V. parahaemolyticus | AQ3321 | − | + |
| 12 | V. parahaemolyticus | AQ3326 | − | + |
| 13 | V. parahaemolyticus | AQ3331 | − | + |
| 14 | V. parahaemolyticus | AQ3343 | − | + |
| 15 | V. parahaemolyticus | AQ3345 | − | + |
| 16 | V. parahaemolyticus | AQ3346 | − | + |
| 17 | V. parahaemolyticus | AQ3354 | − | + |
| 18 | V. parahaemolyticus | AQ3360 | − | + |
| 19 | V. parahaemolyticus | AQ3627 | − | + |
| 20 | V. parahaemolyticus | AQ3629 | − | + |
| 21 | V. parahaemolyticus | AQ3633 | − | + |
| 22 | V. parahaemolyticus | AQ3634 | − | + |
| 23 | V. parahaemolyticus | BB22 | − | + |
| 24 | V. parahaemolyticus | ML34 | − | + |
| 25 | V. parahaemolyticus | ML159 | − | + |
| 26 | V. parahaemolyticus | ML1017 | − | + |
| 27 | V. parahaemolyticus | MY67-6 | − | + |
| 28 | V. parahaemolyticus | MY73-2 | − | + |
| 29 | V. parahaemolyticus | OK80-480 | − | + |
| 30 | V. parahaemolyticus | OKA80-214 | − | + |
| 31 | V. parahaemolyticus | OKA80-232 | − | + |
| 32 | V. parahaemolyticus | S53 | − | + |
| 33 | V. parahaemolyticus | RIMD2210521 | − | + |
| 34 | V. parahaemolyticus | AR1-01 | − | + |
| 35 | V. parahaemolyticus | AR3-02 | − | + |
| 36 | V. parahaemolyticus | AR4-01 | − | + |
| 37 | V. parahaemolybcus | AR4-02 | − | + |
| 38 | V. parahaemolyticus | AR6-01 | − | + |
| 39 | V. parahaemolyticus | AR6-02 | − | + |
| 40 | V. parahaemolyticus | AR7-01 | − | + |
| 41 | V. parahaemolyticus | KB1-01 | − | + |
| 42 | V. parahaemolyticus | KB1-03 | − | + |

For evaluation of the assay systems based on PCR, dilutions of the genomic DNA of Vibrio parahaemolyticus ATCC17802 strain were prepared and used as the template for PCR-based amplification. Even in the dilution containing only 1 ng of the genomic DNA, detection was possible by amplification using the primers VP1 and VP2. For enhancement of the sensitivity from the ng level up to the pg level, DNA after electrophoresis was subjected to the Southern blotting. The dilution of cultivated Vibrio parahaemolyticus ATCC17802 cells was used for amplification with the primer described above, where the detection limit was about 1 cfu/reaction tube. That is, the detection limit based on PCR was 1 cfu/10 μl or $10^3$ cfu/ml. Detection by plating or by use of a selective agar medium has a sensitivity capable of detecting one liable cell but requires much labor and much time.

The assay methods based on PCR are superior to the conventional detection methods from the viewpoint of the balance among the speed, sensitivity, and specificity which is essential for the method of detection of bacteria, and thus useful.

BEST EMBODIMENTS OF THE INVENTION

This invention is explained with Examples in the following. The Examples show the mode of working of the invention, and do not limit the invention at all.

EXAMPLE 1
Conventional method of isolation of Vibrio parahaemolyticus in food To 25 g of a food specimen, was added the alkaline peptone water [manufactured by Nissui Pharmaceutical Co., Ltd.] followed by inoculation with Vibrio parahaemolyticus ATCC17802 and incubation at 37° C. for 18 hours. One loopful amount of the culture was inoculated into the TCBS agar medium by streaking and incubated at 37° C. for 24 hours. All of green colonies were isolated further with the $T_1N_1$ agar medium (distilled water containing 1% of Bacto tryptone, 1% of NaCl, and 1.5% of agar). Sufficiently isolated colonies were subjected to biochemical examinations. The strains that showed the following properties were identified as typical Vibrio parahaemolyticus: positive tests for oxidase, lysine decarboxylase, ornithine decarboxylase, gellatinase, lipase, and chitinase; indole producing; viable at the salt concentration of 0.5 to 8% at 42° C. sensitive to O/129 (150 μg); producing acids from glucose, mannitol, and mannose; negative tests for arginine dehydrogenase and arginase; not viable at, salt concentration of 0%; and producing no acid from sucrose, lactose or salicin.

EXAMPLE 2
Isolation of chromosomal DNA

A Vibrio parahaemolyticus strain was cultured by shaking in the TSB medium (manufactured by Eiken Chemical Co., Ltd.) at 37° C. for about 24 hours. Cells were collected by centrifugation (manufactured by Tomy Seiko Co., Ltd.) (15,000 rpm, 15 minutes, 4° C.), and suspended in 10 ml of sterile TE buffer (10 mM Tris, 1 mM EDTA, pH 8.0). Cells were lysed by lysozyme (final concentration 1 mg/ml; manufactured by Wako Pure Chemical Industries, Ltd.), and maintained at 37° C. for 20 minutes while being shaken gently. To the cell lyzate was added SDS (final concentration 0.5%) and the mixture was incubated at 65° C. For degradation of protein and RNA, were added proteinase K (final concentration 500 μg/ml) and RNase (final concentration 5 μg/ml), and the mixture was incubated at 37° C. for 30 minutes and for 60 minutes, respectively. The samples were extracted three times with buffer saturated phenol (GIBCO/BRL), once with phenol: chloroform (1:1) and once with chloroform: isoamylalcohol (24:1). Clear supernatant was obtained by centrifugation of the extract and DNA was precipitated by addition of two volumes of ice-cooled ethanol: 3M sodium acetate (10:1). The reaction mixture was kept overnight at −20° C. The DNA precipitate was concentrated by centrifugation, and ethanol was evaporated off under reduced pressure. The dried DNA was dissolved in the TE buffer, which was used as the DNA template. The purity of DNA was determined by electrophoresis on agarose gel, and the concentration of DNA was determined with the spectrophotometer.

EXAMPLE 3
Assay based on PCR

Preparation of specimens

All cells including also those not used for extraction of DNA were used as the template. Fresh cells grown on agar media were used. Cells grown on liquid media were used after separation of cells by centrifugation followed by washing once with PBS buffer (pH 7.5), and a suitable number of resultant cells were used. In some cases, DNA extracted with phenol-chloroform was used as the template of PCR amplification.

PCR amplification conditions

PCR assay was carried out with a DNA Thermal Cycler (Perkin Elmer Corp.). One hundred microliter of the reaction mixture (Tris-HCL 100 mM, $MgCl_2$ 15 mM, KCl 500 mM, pH 8.3) contains 100 ng of genomic DNA, 200 μM of dNTPs, and 1 μM of primer. DNA degeneration, annealing, and DNA extension were carried out at 94° C. for 60 seconds, at 60° C. for 60 seconds, and at 72° C. for 120 seconds, respectively, and a total of 30 cycles of amplification were performed. Following amplification, detection was made by gel electrophoresis. Twenty microliter of the sample was subjected to electrophoresis on agarose gel (1% agarose, SeaKem ME, FMC Bioproducts, Rockland, Me.). The DNA band was stained with the ethidium bromide solution for 10 minutes and observed under ultraviolet irradiation.

INDUSTRIAL APPLICABILITY

A primer which reacts specifically with a gyrB gene of *Vibrio parahaemolyticus* to thereby differentiate and identify the same among other Vibrios and strains other than the genus Vibrio could be provided.

The *Vibrio parahaemolyticus*-specific primer serves to detect 285-bp gyrB gene fragments specific for this Vibrio by the PCR method without the necessity for DNA extraction or like operations from bacterial cells.

What is claimed is:

1. An oligonucleotide comprising a nucleotide sequence which specifically hybridizes to and specifically amplifies the nucleotide sequence of SEQ ID NO: 1.

2. The oligonucleotide of claim 1, wherein said nucleotide sequence of said oligonucleotide does not hybridize to and amplify the nucleotide sequence of SEQ ID NO:3.

3. A method of detecting *Vibrio parahaemolyticus* in a specimen, comprising
   (a) preparing a primer set comprising a first oligonucleotide and a second oligonucleotide according to any one of claims 1 or 2,
   (b) amplifying a DNA gyrase subunit B gene sequence contained in the specimen using said primer set of step (a), and
   (c) detecting amplification products produced in step (b), wherein the presence of said amplification products is indicative of the presence of *Vibrio parahaemolyticus* in the specimen.

4. An oligonucleotide comprising SEQ ID NO:5 or SEQ ID NO:6.

5. The oligonucleotide of claim 4, consisting of SEQ ID NO:5 or SEQ ID NO:6.

6. A method of detecting *Vibrio parahaemolyticus* in a specimen, comprising
   (a) preparing a primer set comprising a first oligonucleotide comprising SEQ ID NO:5 or consisting of SEQ ID NO:5 and a second oligonucleotide comprising SEQ ID NO:6 or consisting of SEQ ID NO:6,
   (b) amplifying a DNA gyrase subunit B gene sequence contained in the specimen using the primer set of step (a), and
   (c) detecting amplification products produced in step (b), wherein the presence of said amplification products is indicative of the presence of *Vibrio parahaemolyticus* in the specimen.

* * * * *

SEQUENCE LISTING

```
<160> NUMBER OF SEQ ID NOS: 6

<210> SEQ ID NO 1
<211> LENGTH: 1258
<212> TYPE: DNA
<213> ORGANISM: Vibrio parahaemolyticus
<220> FEATURE:
<221> NAME/KEY: gene
<222> LOCATION: (1)..(1258)

<400> SEQUENCE: 1
gaagtcatca tgaccgttct gcatgccggt ggtaaattcg atgataactc gtacaaagta      60
tcaggcggtc ttcacggcgt gggtgtttcg gtagtaaacg cactgtcaga aaaagtggta     120
ctaaccatcc atcgtggcgg tcatatccac acgcaaactt accgtcatgg tgagcctgaa     180
acgcctctag cggttgtggg tgatgcggat aaaactggta cacaaattcg tttctggcca     240
agtgcagaaa ctttctctaa cactgaattc cattacgaca tcctagcaaa acgtctgcgt     300
gagctatcgt tcttgaactc aggcgtttct atcaagctta ttgatgagcg cgaagcggac     360
aagcaagatc acttcatgta tgaaggtggt attcaagcgt tcgttcagca cttaaacacc     420
aacaaaacac caatcatcga gaaaatcttc cacttcgact tagaacgtga agacggcatt     480
tcggtagaag tggcaatgca gtggaacgat ggtttccaag agaacatctt ctgtttcacc     540
aacaacattc cacagcgcga tggtggtact caccttgctg gtttccgtgc ggcaataaca     600
cgtacgctaa acagctttat ggataaagaa ggcttctcga agaaagcgaa aacggcaacg     660
tcaggcgacg atgcgcgtga aggtttgact gccgttgttt cagtaaaagt gcctgatcca     720
aaattctcga gccaaacaaa agacaaactg gtttcttctg aagtgaaatc agcggttgaa     780
tcggcgatgg gtgagaagct atctgagttc ttggtcgaaa acccaagtga agcgaaaatg     840
gtttgttcga aaatcatcga tgcagcacgt gcacgtgaag ccgcacgtaa agcgcgtgaa     900
atgactcgtc gtaaaggcgc gctagaccta gcaggcctac caggcaaact tgcagactgt     960
caggaaaaag atccggcact ctctgaacta tacattgtgg agggtgactc tgcgggtggt    1020
tcagctaagc agggtcgtaa tcgtaagaat caggcaatcc taccactgaa aggtaagatc    1080
ctgaacgtag aaaaagcacg tttcgacaag atgttgtctt cgcaagaagt tgcaacgctt    1140
attacagcac ttggctgtgg tatcggtcgt gacgagcaca acccggacaa actgcgttac    1200
cacaacatca tcatcatgac cgacgcagac gtagaggctc gcacatccgt accctgct      1258

<210> SEQ ID NO 2
<211> LENGTH: 419
<212> TYPE: PRT
<213> ORGANISM: Vibrio parahaemolyticus

<400> SEQUENCE: 2
```

-continued

```
Glu Val Ile Met Thr Val Leu His Ala Gly Gly Lys Phe Asp Asp Asn
 1               5                  10                  15

Ser Tyr Lys Val Ser Gly Gly Leu His Gly Val Gly Val Ser Val Val
             20                  25                  30

Asn Ala Leu Ser Glu Lys Val Leu Thr Ile His Arg Gly Gly His
             35                  40                  45

Ile His Thr Gln Thr Tyr Arg His Gly Glu Pro Glu Thr Pro Leu Ala
     50                  55                  60

Val Val Gly Asp Ala Asp Lys Thr Gly Thr Gln Ile Arg Phe Trp Pro
 65              70                  75                  80

Ser Ala Glu Thr Phe Ser Asn Thr Glu Phe His Tyr Asp Ile Leu Ala
                 85                  90                  95

Lys Arg Leu Arg Glu Leu Ser Phe Leu Asn Ser Gly Val Ser Ile Lys
             100                 105                 110

Leu Ile Asp Glu Arg Glu Ala Asp Lys Gln Asp His Phe Met Tyr Glu
             115                 120                 125

Gly Gly Ile Gln Ala Phe Val Gln His Leu Asn Thr Asn Lys Thr Pro
 130                 135                 140

Ile Ile Glu Lys Ile Phe His Phe Asp Leu Glu Arg Glu Asp Gly Ile
145                 150                 155                 160

Ser Val Glu Val Ala Met Gln Trp Asn Asp Gly Phe Gln Glu Asn Ile
                 165                 170                 175

Phe Cys Phe Thr Asn Asn Ile Pro Gln Arg Asp Gly Gly Thr His Leu
                 180                 185                 190

Ala Gly Phe Arg Ala Ala Ile Thr Arg Thr Leu Asn Ser Phe Met Asp
                 195                 200                 205

Lys Glu Gly Phe Ser Lys Lys Ala Lys Thr Ala Thr Ser Gly Asp Asp
             210                 215                 220

Ala Arg Glu Gly Leu Thr Ala Val Val Ser Val Lys Val Pro Asp Pro
225                 230                 235                 240

Lys Phe Ser Ser Gln Thr Lys Asp Lys Leu Val Ser Ser Glu Val Lys
                 245                 250                 255

Ser Ala Val Glu Ser Ala Met Gly Glu Lys Leu Ser Glu Phe Leu Val
                 260                 265                 270

Glu Asn Pro Ser Glu Ala Lys Met Val Cys Ser Lys Ile Ile Asp Ala
             275                 280                 285

Ala Arg Ala Arg Glu Ala Ala Arg Lys Ala Arg Glu Met Thr Arg Arg
             290                 295                 300

Lys Gly Ala Leu Asp Leu Ala Gly Leu Pro Gly Lys Leu Ala Asp Cys
305                 310                 315                 320

Gln Glu Lys Asp Pro Ala Leu Ser Glu Leu Tyr Ile Val Glu Gly Asp
                 325                 330                 335

Ser Ala Gly Gly Ser Ala Lys Gln Gly Arg Asn Arg Lys Asn Gln Ala
             340                 345                 350

Ile Leu Pro Leu Lys Gly Lys Ile Leu Asn Val Glu Lys Ala Arg Phe
             355                 360                 365

Asp Lys Met Leu Ser Ser Gln Glu Val Ala Thr Leu Ile Thr Ala Leu
     370                 375                 380

Gly Cys Gly Ile Gly Arg Asp Glu His Asn Pro Asp Lys Leu Arg Tyr
385                 390                 395                 400

His Asn Ile Ile Ile Met Thr Asp Ala Asp Val Glu Ala Arg Thr Ser
                 405                 410                 415

Val Pro Cys
```

-continued

<210> SEQ ID NO 3
<211> LENGTH: 1258
<212> TYPE: DNA
<213> ORGANISM: Vibrio parahaemolyticus
<220> FEATURE:
<221> NAME/KEY: gene
<222> LOCATION: (1)..(1258)

<400> SEQUENCE: 3

```
gaagtcatca tgaccgttct gcatgcaggt ggtaaattcg acgataacac aaacaaatta      60
tcgggtggtc tccacggggt acgtgtctca gtaataaacg cactatcaga gaaagttgag     120
ctaacgattc atcgtggtgg ccatatccat acgcaaacct accgccatgg tgagcctgca     180
acgccactag ccgttgtggg tgatacggat aaaaccggta cacaaattcg tttctggcca     240
agtgccgaga cgttctctaa cactgagttc cactatgaca ttctggcgaa acgcctgcgt     300
gaactgtcat tcctgaactc tggtgtgtcg atcaaattgg ttgatgaacg tgaagcggac     360
aaacatgatc acttcatgta tgaaggtggt attcaagcgt tcgttgatca cctaaacacc     420
aacaaaacgc caatcatcga gagggtcttc cactttaact ctgagcgtga agacggcatt     480
tcagttgaag tggcgatgca atggaacgat ggtttccaag agaacatctt ctgctttacc     540
aacaatatcc cacagcgtga tggtggtact caccttgctg gtttccgtgc tgcgctaaca     600
cgtacattga acagctttat ggataaagaa ggtttctcga agaaagcgaa acagcgact      660
tcaggcgacg atgcgcgtga aggtctaact gcggttgttt cggtgaaagt gcctgatcct     720
aagttctcaa gccaaacaaa agacaaactg gtttcttctg aagtgaaatc agctgttgag     780
tctgcaatgg gtgaaaaact gtctgagttc ttgattgaga cccgacaga agcgaagatg      840
gtttgttcga aaatcatcaa tgcagcacgt gcatctgaag cagcgcctaa agctcgtgaa     900
atgacgcgcc gtaaaggtgc actagaccta gcaggccttc caggtaaagt tgcagactgt     960
caggaaaaag atccggcact ctttgaacta tacatagtgg agggtgaatc ggcaggcggt    1020
tccgcaaaac aaggccgtaa ccgtaagaac caagcgatca caccgctaaa aggtaagatt    1080
cttaacgtag aaaaagcacg tttcgacaag atgctatctt ctctagaagt agtaacactg    1140
atcaccgcat taggttgtgg tatcggtcgt gacgaggaca acccgacaa gcctcgggac     1200
cacaacataa tcatcatgac cgacgcagac gtagaggctc gcacatccgt accctgct     1258
```

<210> SEQ ID NO 4
<211> LENGTH: 419
<212> TYPE: PRT
<213> ORGANISM: Vibrio parahaemolyticus

<400> SEQUENCE: 4

```
Glu Val Ile Met Thr Val Leu His Ala Gly Gly Lys Phe Asp Asp Asn
  1               5                  10                  15

Thr Asn Lys Leu Ser Gly Gly Leu His Gly Val Arg Val Ser Val Ile
             20                  25                  30

Asn Ala Leu Ser Glu Lys Val Glu Leu Thr Ile His Arg Gly Gly His
         35                  40                  45

Ile His Thr Gln Thr Tyr Arg His Gly Glu Pro Ala Thr Pro Leu Ala
     50                  55                  60

Val Val Gly Asp Thr Asp Lys Thr Gly Thr Gln Ile Arg Phe Trp Pro
 65                  70                  75                  80

Ser Ala Glu Thr Phe Ser Asn Thr Glu Phe His Tyr Asp Ile Leu Ala
                 85                  90                  95
```

-continued

```
Lys Arg Leu Arg Glu Leu Ser Phe Leu Asn Ser Gly Val Ser Ile Lys
            100                 105                 110

Leu Val Asp Glu Arg Glu Ala Asp Lys His Asp His Phe Met Tyr Glu
        115                 120                 125

Gly Gly Ile Gln Ala Phe Val Asp His Leu Asn Thr Asn Lys Thr Pro
    130                 135                 140

Ile Ile Glu Arg Val Phe His Phe Asn Ser Glu Arg Glu Asp Gly Ile
145                 150                 155                 160

Ser Val Glu Val Ala Met Gln Trp Asn Asp Gly Phe Gln Glu Asn Ile
                165                 170                 175

Phe Cys Phe Thr Asn Asn Ile Pro Gln Arg Asp Gly Gly Thr His Leu
            180                 185                 190

Ala Gly Phe Arg Ala Ala Leu Thr Arg Thr Leu Asn Ser Phe Met Asp
        195                 200                 205

Lys Glu Gly Phe Ser Lys Ala Lys Thr Ala Thr Ser Gly Asp Asp
    210                 215                 220

Ala Arg Glu Gly Leu Thr Ala Val Val Ser Val Lys Val Pro Asp Pro
225                 230                 235                 240

Lys Phe Ser Ser Gln Thr Lys Asp Lys Leu Val Ser Ser Glu Val Lys
                245                 250                 255

Ser Ala Val Glu Ser Ala Met Gly Glu Lys Leu Ser Glu Phe Leu Ile
            260                 265                 270

Glu Asn Pro Thr Glu Ala Lys Met Val Cys Ser Lys Ile Ile Asn Ala
        275                 280                 285

Ala Arg Ala Ser Glu Ala Ala Pro Lys Ala Arg Glu Met Thr Arg Arg
    290                 295                 300

Lys Gly Ala Leu Asp Leu Ala Gly Leu Pro Gly Lys Val Ala Asp Cys
305                 310                 315                 320

Gln Glu Lys Asp Pro Ala Leu Phe Glu Leu Tyr Ile Val Glu Gly Glu
                325                 330                 335

Ser Ala Gly Gly Ser Ala Lys Gln Gly Arg Asn Arg Lys Asn Gln Ala
            340                 345                 350

Ile Thr Pro Leu Lys Gly Lys Ile Leu Asn Val Glu Lys Ala Arg Phe
        355                 360                 365

Asp Lys Met Leu Ser Ser Leu Glu Val Val Thr Leu Ile Thr Ala Leu
    370                 375                 380

Gly Cys Gly Ile Gly Arg Asp Glu Asp Asn Pro Asp Lys Pro Arg Asp
385                 390                 395                 400

His Asn Ile Ile Ile Met Thr Asp Ala Asp Val Glu Ala Arg Thr Ser
                405                 410                 415

Val Pro Cys

<210> SEQ ID NO 5
<211> LENGTH: 21
<212> TYPE: DNA
<213> ORGANISM: Vibrio parahaemolyticus

<400> SEQUENCE: 5
cggcgtgggt gtttcggtag t                                           21
```

-continued

```
<210> SEQ ID NO 6
<211> LENGTH: 21
<212> TYPE: DNA
<213> ORGANISM: Vibrio parahaemolyticus

<400> SEQUENCE: 6
tccgcttcgc gctcatcaat a                                              21
```